(12) United States Patent
Argentine

(10) Patent No.: US 8,623,064 B2
(45) Date of Patent: Jan. 7, 2014

(54) STENT GRAFT DELIVERY SYSTEM AND METHOD OF USE

(75) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 536 days.

(21) Appl. No.: 12/771,092

(22) Filed: Apr. 30, 2010

(65) Prior Publication Data

US 2011/0270372 A1 Nov. 3, 2011

(51) Int. Cl.
*A61F 2/06* (2013.01)

(52) U.S. Cl.
USPC .......................................... 623/1.11; 623/1.23

(58) Field of Classification Search
USPC .............. 623/1.11–1.12, 1.23, 2.11; 606/108
See application file for complete search history.

(56) References Cited

U.S. PATENT DOCUMENTS

| | | | |
|---|---|---|---|
| 1,827,497 A | 10/1931 | Varney | |
| 4,646,751 A * | 3/1987 | Maslanka | 600/564 |
| 4,723,938 A | 2/1988 | Goodin et al. | |
| 4,832,692 A | 5/1989 | Box et al. | |
| 4,990,151 A | 2/1991 | Wallsten | |
| 5,017,259 A * | 5/1991 | Kohsai | 156/294 |
| 5,137,514 A | 8/1992 | Ryan | |
| 5,197,971 A | 3/1993 | Bonutti | |
| 5,215,523 A | 6/1993 | Williams et al. | |
| 5,224,954 A * | 7/1993 | Watts et al. | 606/205 |
| 5,259,838 A | 11/1993 | Taylor et al. | |
| 5,263,969 A | 11/1993 | Philips | |
| 5,344,426 A | 9/1994 | Lau et al. | |
| 5,345,927 A | 9/1994 | Bonutti | |
| 5,358,496 A | 10/1994 | Oritz et al. | |
| 5,415,664 A | 5/1995 | Pinchuk | |
| 5,433,723 A | 7/1995 | Lindenberg et al. | |
| 5,449,344 A | 9/1995 | Taylor et al. | |
| 5,462,659 A | 10/1995 | Saxena et al. | |
| 5,507,727 A | 4/1996 | Crainich | |
| 5,507,768 A | 4/1996 | Lau et al. | |
| 5,534,007 A | 7/1996 | St. Germain et al. | |
| 5,571,168 A | 11/1996 | Toro | |
| 5,683,451 A | 11/1997 | Lenker et al. | |
| 5,693,084 A | 12/1997 | Chuter | |
| 5,700,269 A * | 12/1997 | Pinchuk et al. | 606/108 |
| 5,707,376 A | 1/1998 | Kavteladze et al. | |
| 5,713,917 A | 2/1998 | Leonhardt et al. | |
| 5,733,267 A | 3/1998 | Del Toro | |

(Continued)

FOREIGN PATENT DOCUMENTS

| | | |
|---|---|---|
| DE | 20000659 | 5/2001 |
| EP | 1 302 178 | 4/2003 |

(Continued)

*Primary Examiner* — Katherine Dowe
*Assistant Examiner* — Kendra Obu

(57) ABSTRACT

A stent graft delivery system including a tip assembly, a middle member tube, a sheath assembly, a threaded assembly, and a unitary endoseal. The tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first cylindrical portion of the transverse cylindrical endoseal body is disposed in the first sidewall port of the threaded assembly, the second cylindrical portion of the transverse cylindrical endoseal body is disposed in the second sidewall port of the threaded assembly, and the longitudinal endoseal cylindrical body is disposed in the threaded assembly lumen.

20 Claims, 5 Drawing Sheets

(56) References Cited

U.S. PATENT DOCUMENTS

| | | |
|---|---|---|
| 5,733,325 A | 3/1998 | Robinson et al. |
| 5,755,777 A | 5/1998 | Chuter |
| 5,776,142 A | 7/1998 | Gunderson |
| 5,782,855 A | 7/1998 | Lau et al. |
| 5,788,707 A | 8/1998 | Del Toro et al. |
| 5,797,952 A | 8/1998 | Klein |
| 5,824,041 A | 10/1998 | Lenker et al. |
| 5,824,058 A | 10/1998 | Ravenscroft et al. |
| 5,860,955 A | 1/1999 | Wright et al. |
| 5,902,334 A | 5/1999 | Dwyer et al. |
| 5,906,619 A | 5/1999 | Olson et al. |
| 5,935,161 A | 8/1999 | Robinson et al. |
| 5,954,742 A | 9/1999 | Osypka |
| 5,968,052 A | 10/1999 | Sullivan, III et al. |
| 6,042,588 A | 3/2000 | Munsinger et al. |
| 6,077,297 A | 6/2000 | Robinson et al. |
| 6,110,151 A | 8/2000 | Spool et al. |
| 6,117,142 A | 9/2000 | Goodson et al. |
| 6,143,021 A | 11/2000 | Staehle |
| 6,146,415 A | 11/2000 | Fitz |
| 6,251,132 B1 | 6/2001 | Ravenscroft et al. |
| 6,395,017 B1 | 5/2002 | Dwyer et al. |
| 6,468,298 B1 | 10/2002 | Pelton |
| 6,488,700 B2 | 12/2002 | Klumb et al. |
| 6,508,790 B1 | 1/2003 | Lawrence |
| 6,514,261 B1 | 2/2003 | Randall et al. |
| 6,520,986 B2 | 2/2003 | Martin et al. |
| 6,656,212 B2 | 12/2003 | Ravenscroft et al. |
| 6,660,030 B2 * | 12/2003 | Shaolian et al. ............. 623/1.11 |
| 6,676,692 B2 | 1/2004 | Rabkin et al. |
| 6,749,584 B2 * | 6/2004 | Briggs et al. ............. 604/103.05 |
| 6,764,503 B1 | 7/2004 | Ishimaru |
| 6,843,802 B1 | 1/2005 | Villalobos et al. |
| 6,911,039 B2 | 6/2005 | Shiu et al. |
| 7,264,632 B2 | 9/2007 | Wright et al. |
| 7,419,501 B2 * | 9/2008 | Chiu et al. .................. 623/1.12 |
| 7,435,253 B1 | 10/2008 | Hartley et al. |
| 7,803,177 B2 | 9/2010 | Hartley et al. |
| 7,815,671 B2 | 10/2010 | Wright et al. |
| 2002/0004676 A1 | 1/2002 | Berryman et al. |
| 2002/0111666 A1 | 8/2002 | Hart et al. |
| 2003/0074043 A1 | 4/2003 | Thompson |
| 2003/0074045 A1 | 4/2003 | Buzzard et al. |
| 2003/0199966 A1 | 10/2003 | Shiu et al. |
| 2003/0233140 A1 | 12/2003 | Hartley et al. |
| 2004/0093063 A1 | 5/2004 | Wright et al. |
| 2004/0127912 A1 | 7/2004 | Rabkin et al. |
| 2005/0080476 A1 | 4/2005 | Gunderson et al. |
| 2005/0085888 A1 | 4/2005 | Andreas et al. |
| 2005/0137612 A1 | 6/2005 | Assell et al. |
| 2005/0228475 A1 | 10/2005 | Keeble et al. |
| 2006/0085057 A1 | 4/2006 | George |
| 2006/0276872 A1 | 12/2006 | Arbefeuille et al. |
| 2006/0282150 A1 * | 12/2006 | Olson et al. .................. 623/1.11 |
| 2007/0021777 A1 * | 1/2007 | Fowler .......................... 606/205 |
| 2007/0135818 A1 | 6/2007 | Moore et al. |
| 2007/0156224 A1 * | 7/2007 | Cioanta et al. ............... 623/1.11 |
| 2007/0219616 A1 | 9/2007 | Modesitt et al. |
| 2008/0077227 A1 | 3/2008 | Ouellette et al. |
| 2008/0255427 A1 * | 10/2008 | Satake et al. .................. 600/204 |
| 2008/0255651 A1 | 10/2008 | Dwork |
| 2008/0262590 A1 | 10/2008 | Murray |
| 2009/0171432 A1 * | 7/2009 | Von Segesser et al. ...... 623/1.11 |
| 2009/0254165 A1 | 10/2009 | Tabor et al. |
| 2009/0319018 A1 | 12/2009 | Moehl et al. |
| 2010/0030255 A1 | 2/2010 | Berra et al. |
| 2010/0234933 A1 * | 9/2010 | Punga et al. .................. 623/1.12 |
| 2011/0257718 A1 | 10/2011 | Argentine |
| 2011/0270371 A1 | 11/2011 | Argentine |
| 2011/0270372 A1 | 11/2011 | Argentine |

FOREIGN PATENT DOCUMENTS

| | | |
|---|---|---|
| EP | 1358903 | 12/2004 |
| FR | 2779939 | 6/1998 |
| WO | WO96/18361 | 6/1996 |
| WO | WO 2005/067819 | 7/2005 |

* cited by examiner

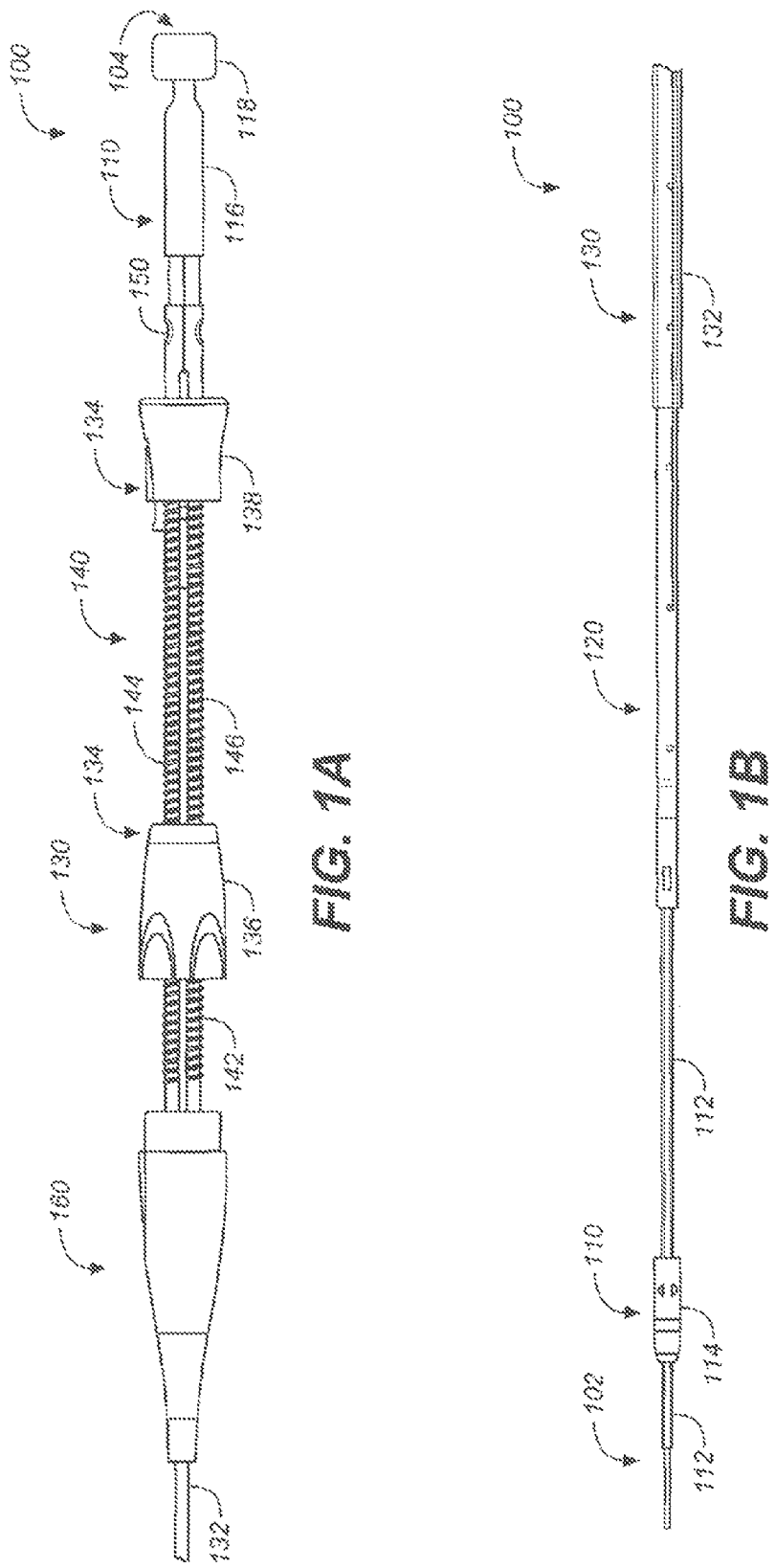

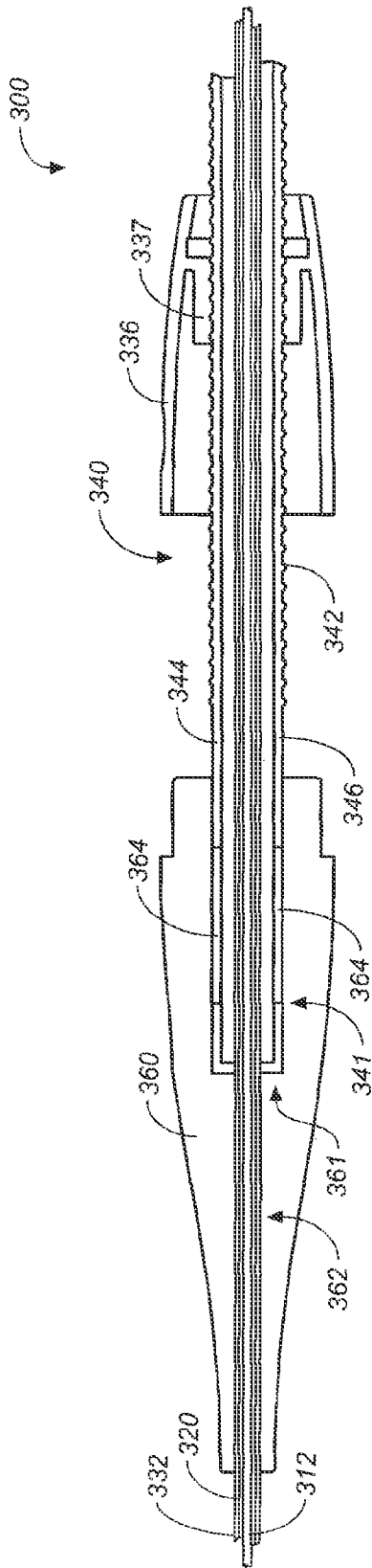
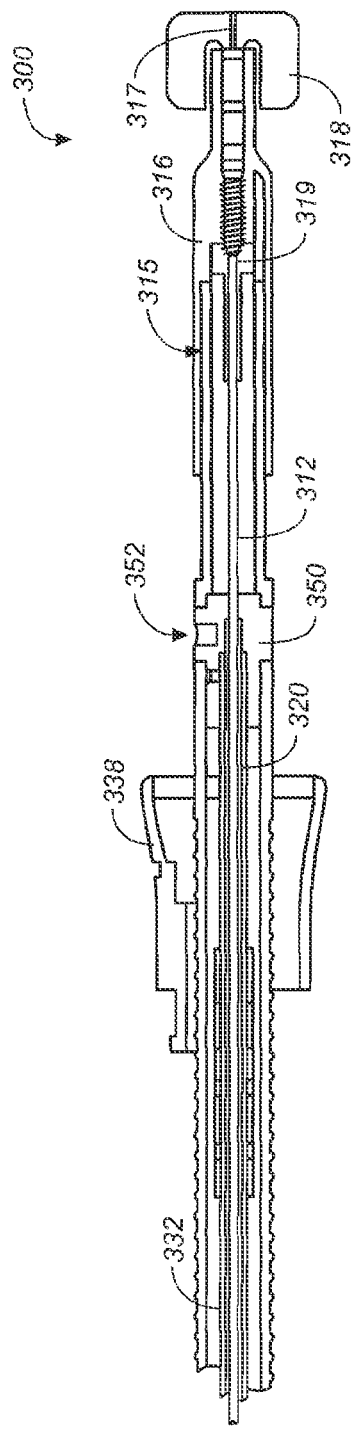
FIG. 3A
FIG. 3B

STENT GRAFT DELIVERY SYSTEM AND METHOD OF USE

TECHNICAL FIELD

The technical field of this disclosure is medical implantation devices, particularly, a stent graft delivery system.

BACKGROUND OF THE INVENTION

Stent grafts have been developed for the treatment of abdominal and thoracic aortic aneurysms. An abdominal aortic aneurysm is a bulge that forms in the wall of the abdominal aorta, which is the main vessel of the arterial system of the body that extends through the abdomen. A thoracic aortic aneurysm is a bulge that forms in the wall of the thoracic aorta, which is the main vessel of the arterial system of the body that extends through the chest. Aortic aneurysms can lose elasticity over time and rupture under normal blood pressure. A stent graft is a woven tube (graft) supported by a tubular metal stent. The stent graft is placed inside and spanning an aneurysmal vessel to exclude the aortic aneurysm from normal blood flow and reduce pressure on the aneurysmal vessel.

Stent graft delivery systems are used to deliver the stent grafts to a deployment location inside the aorta. The stent graft can be inserted through a femoral artery and into the aorta. The stent graft can be enclosed within a sheath until the stent graft is in position at the deployment location, and then the sheath can be retracted to allow the stent graft to expand. The stent graft delivery system includes a number of complex parts which are needed to allow a clinician to manipulate the stent graft to be deployed remotely.

Presently, stent graft delivery systems include a large number of separate parts to meet the various performance requirements for stent graft deployment. For example, the tubes in the stent graft delivery systems must include homeostatic seals to reduce blood loss during the procedure. The tubes must also be flushable to allow filling with fluid before the procedure to prevent air delivery into the vessels. The tubes and other parts must also be fixed or terminated in relation to the associated parts so that the parts can be moveable or fixed to perform their functions. Unfortunately, the large number of separate parts increases manufacturing and inventory costs. Assembly time increases, increasing cost.

It would be desirable to have a stent graft delivery system that would overcome the above disadvantages.

SUMMARY OF THE INVENTION

One aspect according to the present invention provides stent graft delivery system including a tip assembly having a tip tube; a middle member tube having a middle member proximal end and defining a middle member lumen, the tip tube being disposed in and longitudinally slideable within the middle member lumen; a sheath assembly having a sheath tube and a sheath handle operably connected to a sheath tube proximal end, the sheath tube defining a sheath lumen, the middle member tube being disposed in and longitudinally slideable within the sheath lumen; a threaded assembly having an exterior thread, and defining a threaded assembly lumen, a first sidewall port, and a second sidewall port; and a unitary endoseal having an longitudinal cylindrical endoseal body and a transverse cylindrical endoseal body transverse to the longitudinal cylindrical endoseal body, the longitudinal endoseal cylindrical body defining an endoseal lumen having a proximal portion, a middle portion, and a distal portion, the transverse cylindrical endoseal body having a first cylindrical portion and a second cylindrical portion. The tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first cylindrical portion of the transverse cylindrical endoseal body is disposed in the first sidewall port of the threaded assembly, the second cylindrical portion of the transverse cylindrical endoseal body is disposed in the second sidewall port of the threaded assembly, and the longitudinal endoseal cylindrical body is disposed in the threaded assembly lumen. The sheath handle engages the exterior thread of the threaded assembly in a first configuration to move the sheath tube longitudinally relative to the middle member tube and tip tube by rotation of the sheath handle and disengages the exterior thread of the threaded assembly in a second configuration to move the sheath tube longitudinally relative to the middle member tube and tip tube by longitudinal motion of the sheath handle.

Another aspect according to the present invention provides a unitary endoseal for use in a stent graft delivery system having a tip tube; a middle member tube having middle member proximal end and defining a middle member lumen; and a threaded assembly, the threaded assembly defining a threaded assembly lumen, a first sidewall port, and a second sidewall port. The unitary endoseal includes an longitudinal cylindrical endoseal body, the longitudinal endoseal cylindrical body defining an endoseal lumen having a proximal portion, a middle portion, and a distal portion; and a transverse cylindrical endoseal body transverse to the longitudinal cylindrical endoseal body, the transverse cylindrical endoseal body having a first cylindrical portion and a second cylindrical portion. The tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first cylindrical portion of the transverse cylindrical endoseal body is disposed in the first sidewall port of the threaded assembly, the second cylindrical portion of the transverse cylindrical endoseal body is disposed in the second sidewall port of the threaded assembly, and the longitudinal endoseal cylindrical body is disposed in the threaded assembly lumen.

Another aspect according to the present invention provides a stent graft delivery system including a tip assembly having a tip tube; a middle member tube having a middle member proximal end and defining a middle member lumen, the tip tube being disposed in and longitudinally slideable within the middle member lumen; a sheath assembly having a sheath tube and a sheath handle operably connected to a sheath tube proximal end, the sheath tube defining a sheath lumen, the middle member tube being disposed in and longitudinally slideable within the sheath lumen; a threaded assembly having an exterior thread, and defining a threaded assembly lumen, a first sidewall port, and a second sidewall port; and a unitary endoseal having an longitudinal cylindrical endoseal body and a transverse cylindrical endoseal body transverse to the longitudinal cylindrical endoseal body, the longitudinal endoseal cylindrical body having a central axis and defining an endoseal lumen having a proximal portion, a middle portion, and a distal portion, the transverse cylindrical endoseal body having a first cylindrical portion and a second cylindrical portion, the first transverse cylindrical portion defining a tapered flush port tapering inward toward the central axis with a partition between the tapered flush port and the middle portion of the endoseal lumen, the partition defines a slit between the tapered flush port and the middle portion of the endoseal lumen, the middle portion of the endoseal lumen being in communication with the middle member lumen. The tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first cylindrical portion of the transverse cylindrical endoseal body is disposed in the first sidewall port of the threaded assembly, the second cylindrical portion of the transverse cylindrical endoseal body is disposed in the second sidewall port of the threaded assembly, and the longitudinal endoseal cylindrical body is disposed in the threaded assembly lumen; the slit is closed when the flush port is unoccupied; and the slit is open when a flush connector is fully inserted into the flush port The foregoing and other features and advantages will become further apparent from the following detailed description of the embodiments, read in conjunction with the accompanying drawings

BRIEF DESCRIPTION OF THE DRAWINGS

FIGS. 1A & 1B are side views of a stent graft delivery system;
FIGS. 3A & 3B are detailed cross section side views of a stent graft delivery system.

DETAILED DESCRIPTION

Figures 2A, 2B:
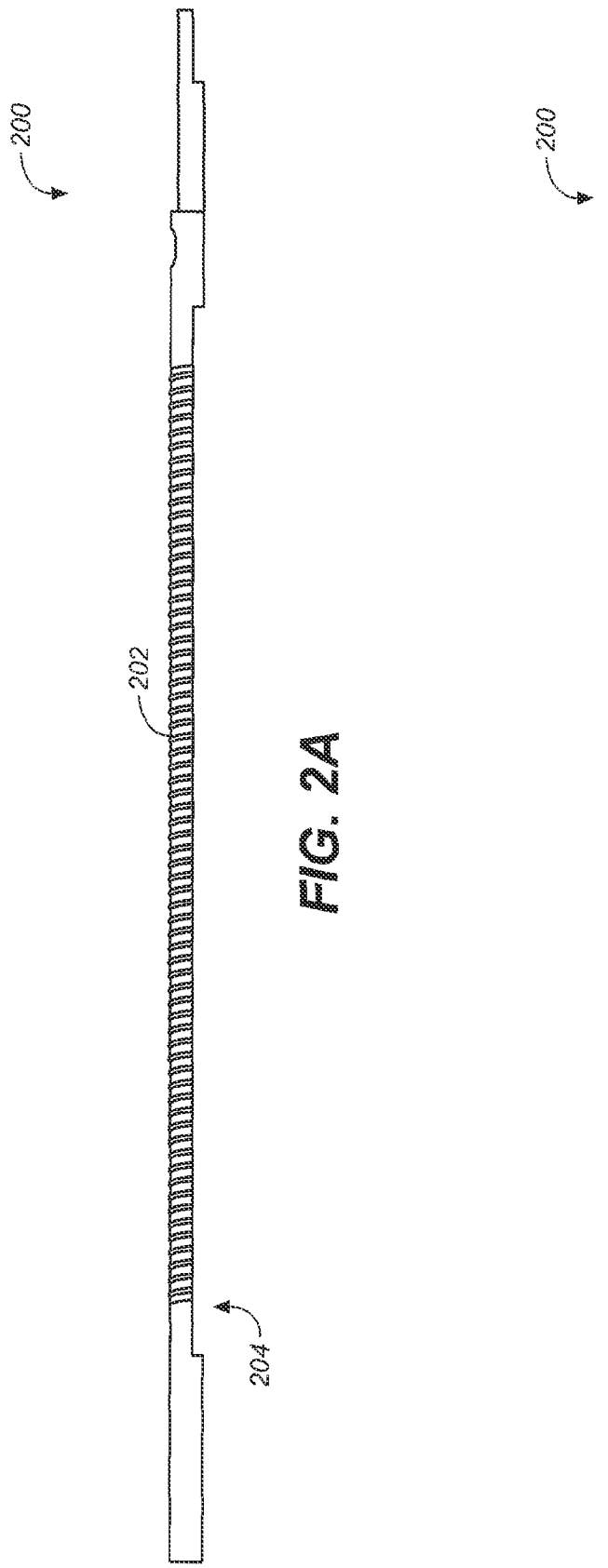
FIGS. 2A & 2B are side and top views, respectively, of a threaded tube portion of a stent graft delivery system.

FIGS. 1A & 1B, in which like elements share like reference numbers, are side views of a stent graft delivery system. The stent graft delivery system 100 includes a tip assembly 110, a middle member tube 120, a sheath assembly 130, a threaded assembly 140, a unitary endoseal 150, and a unitary front grip 160. The distal end 102 of the stent graft delivery system 100 is inserted in a vessel to deliver the stent graft and the proximal end 104 of the stent graft delivery system 100 remains outside the patient. As used herein, distal and proximal are defined from the viewpoint of the operator of the stent graft delivery system 100 with the proximal end 104 nearer the operator.

The tip assembly 110 includes a tip tube 112, a stent graft retainer 114 operably connected to the distal end of the tip tube 112, and a tip handle 118 operably connected to the proximal end of the tip tube 112. The tip tube 112 can define a guide wire lumen longitudinally along the interior of the tip tube 112. The stent graft delivery system 100 can follow a guide wire deployed in the vasculature of the patient to the stent graft deployment site by inserting the guide wire in the guide wire lumen. The middle member tube 120 has a middle member proximal end and defines a middle member lumen longitudinally along the interior of the middle member tube 120. The tip tube 112 is disposed in and longitudinally slideable within the middle member lumen.

The sheath assembly 130 includes a sheath tube 132 and a sheath handle 134 operably connected to a sheath tube proximal end. The sheath tube 132 defines a sheath lumen longitudinally along the interior of the sheath tube 132. The middle member tube 120 is disposed in and longitudinally slideable within the sheath lumen. In this example, the sheath handle 134 includes a rotatable sheath handle 136 and a slideable sheath handle 138, which include complementary fittings so that the rotatable sheath handle 136 and the slideable sheath handle 138 can be connected into a single sheath handle while still allowing rotation of the rotatable sheath handle 136.

The threaded assembly 140 has an exterior thread 142 and defines a threaded assembly lumen, a first sidewall port, and a second sidewall port. The threaded assembly 140 can include first threaded tube portion 144 and a second threaded tube portion 146. The unitary front grip 160 and/or unitary rear grip 116 can press the first threaded tube portion 144 and a second threaded tube portion 146 together to form the threaded assembly 140. The sheath handle 134 engages the exterior thread 142 of the threaded assembly 140 in a first configuration to move the sheath tube 132 longitudinally relative to the middle member tube 120 and tip tube 112 by rotation of the sheath handle 134. The sheath handle 134 disengages the exterior thread 142 of the threaded assembly 140 in a second configuration to move the sheath tube 132 longitudinally relative to the middle member tube 120 and tip tube 112 by longitudinal motion of the sheath handle 134.

The unitary endoseal 150 includes an longitudinal cylindrical endoseal body and a transverse cylindrical endoseal body. Portions of the transverse cylindrical endoseal body are disposed in the first and second sidewall ports of the threaded assembly 140. The longitudinal cylindrical endoseal body is disposed in the lumen of the threaded assembly. The tip tube 112 is disposed in and longitudinally slideable within a portion of an endoseal lumen. The middle member proximal end of the middle member tube 120 is disposed in another portion of the endoseal lumen and fixed to the longitudinal cylindrical endoseal body. As used herein, unitary is defined as being a single, whole part, and not a part assembled from other parts.

The unitary front grip 160 defines a front grip lumen. The first threaded tube portion 144 and the second threaded tube portion 146 are radially pressed together by the unitary front grip 160 in the front grip lumen. The sheath tube 132 is disposed in and longitudinally slideable within a portion of a front grip lumen. The distal end of the threaded assembly 140 is disposed in another portion of the front grip lumen and fixed to the unitary front grip 160. In this example, the unitary front grip 160 has a champagne bottle-shaped exterior. As used herein, unitary is defined as being a single, whole part, and not a part assembled from other parts.

In operation, a stent graft is loaded onto the stent graft delivery system 100 over the tip tube 112 between the stent graft retainer 114 and the middle member tube 120. The sheath tube 132 is advanced distally over the stent graft to the stent graft retainer 114 to locate the stent graft within the lumen of the sheath tube 132 and hold the stent graft in a compressed configuration. The rotatable sheath handle 136 and the slideable sheath handle 138 of the sheath handle 134 are coupled together.

A guide wire is positioned in the vasculature of the patient and the stent graft delivery system 100 advanced through the vasculature over the guide wire until the stent graft is at the deployment site, such as in an aortic aneurysm. The operator grasps the unitary front grip 160 and rotates the rotatable sheath handle 136 using the mechanical advantage produced by the motion along the screw threads to gradually withdraw the sheath tube 132 to release a distal portion of the stent graft. When the distal portion of the stent graft is satisfactorily deployed, the rotatable sheath handle 136 and the slideable sheath handle 138 can be uncoupled and the operator can slide the slideable sheath handle 138 longitudinally using direct linear longitudinal motion to withdraw the sheath tube 132 to deploy the remaining portion of the stent graft. When the whole stent graft has been deployed, the operator is now ready to release the Tip Capture which has been holding the struts of the stent in abeyance. This is accomplished by pushing the unitary rear grip 116 forward which moves the stent graft retainer 114 off the stent struts allowing them to embed into the wall of the vessel fixing the device. With the stent graft deployed the Tip Capture Mechanism is prepared for retraction by pulling the unitary rear grip 116 back into its original position. This done, the entire Delivery System may be removed from the vasculature.

FIGS. 2A & 2B, in which like elements share like reference numbers, are side and top views, respectively, of a threaded tube portion of a stent graft delivery system. A pair of threaded tube portions are combined to form a threaded assembly. The threaded tube portion 200 includes an exterior thread 202 that can be engaged by the sheath handle 134 to gradually move the sheath longitudinally by rotation of the sheath handle. The sheath moves within the threaded assembly lumen defined within the pair of threaded tube portions. In one embodiment, the threaded tube portion 200 includes an edge slot 204 to allow a portion of the sheath handle (e.g., ribs or splines) to pass from outside the threaded assembly and connect to the sheath within the threaded assembly lumen. The threaded tube portion 200 can also define a sidewall port 206 and/or a front grip alignment slot 208. The sidewall ports receive a portion of the unitary endoseal, which helps to align the threaded tube portions to each other to form the threaded assembly and can provide access for flushing the middle member lumen. The front grip alignment slots receive a complementarily shaped portion of the unitary front grip to align and prevent rotation of the unitary front grip relative to the threaded tube portion when a differential torque is applied between the two.

FIGS. 3A & 3B, in which like elements share like reference numbers, are detailed cross section side views of a stent graft delivery system. In the stent graft delivery system 300, the tip tube 312 is disposed in the middle member tube 320, which is disposed in the sheath tube 332. The proximal end of the tip tube 312 terminates at a connection 319 to the tip handle 318 with the guide wire lumen continuing through the tip handle 318. The tip tube 312 enters the middle member tube 320 at the unitary endoseal 350. The proximal end of the middle member tube 320 terminates at the unitary endoseal 350, where the middle member tube 320 receives and fluid tightly slidably seals with the tip tube 312. A flush port 352 defined by the middle member tube 320 is in fluid communication with the middle member lumen when a flush connector is inserted into the flush port 352 to allow flushing of the middle member lumen. The proximal end of the sheath tube 332 terminates at the slideable sheath handle 338. The sheath tube 332 is slideable within the proximal portion 362 of the front grip defined by the unitary front grip 360. Alignment tabs 364 in the unitary front grip 360 extend into front grip alignment slots 341 in the first threaded tube portion 344 and second threaded tube portion 346.

An inside threaded portion 337 of the rotatable sheath handle 336 engages the exterior thread 342 of the threaded assembly 340. When the rotatable sheath handle 336 and the slideable sheath handle 338 are coupled, the rotation of the rotatable sheath handle 336 moves the slideable sheath handle 338 longitudinally, simultaneously moving the sheath tube 332. When the rotatable sheath handle 336 and the slideable sheath handle 338 are uncoupled, the longitudinal motion of the slideable sheath handle 338 moves the sheath tube 332 longitudinally, independent of the rotatable sheath handle 336. Thus, the sheath handle engages the exterior threads in a first configuration with the rotatable sheath handle 336 and the slideable sheath handle 338 coupled and disengages from mechanical coupling with the exterior threads in a second configuration with the rotatable sheath handle 336 and the slideable sheath handle 338 uncoupled. Those skilled in the art will appreciate that the action of the rotatable sheath handle and slideable sheath handle are exemplary and that the longitudinal displacement of the sheath tube can be accomplished with other sheath handle mechanisms as desired for a particular application.

Figure 4A:
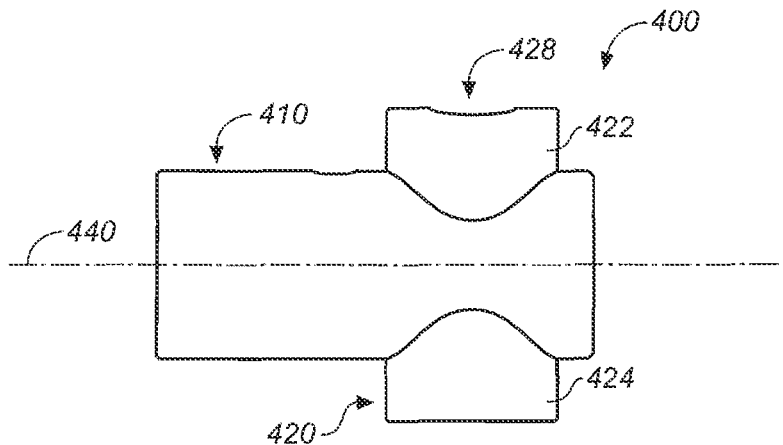
FIGS. 4A-4E are various views of a unitary endoseal of a stent graft delivery system.
Figure 4B:
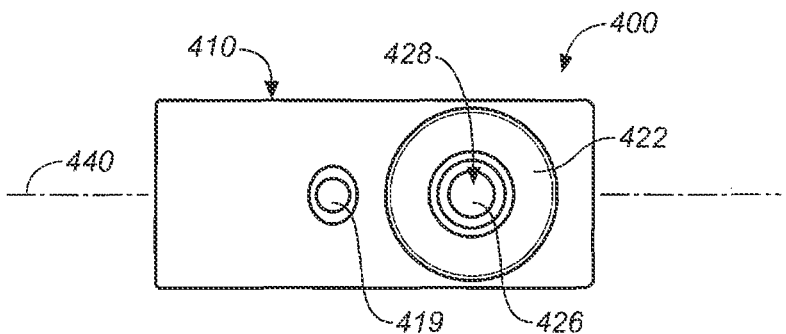
Figure 4C:
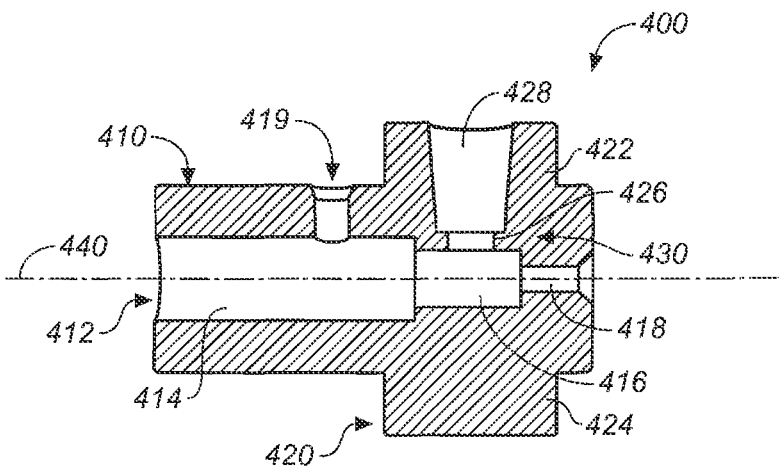
Figure 4D:
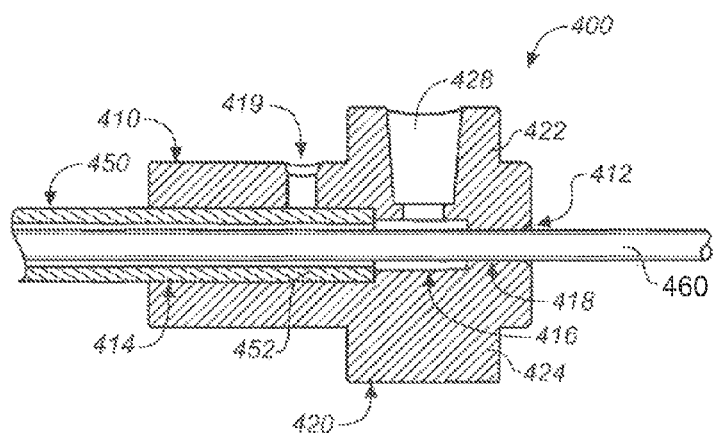
Figure 4E:
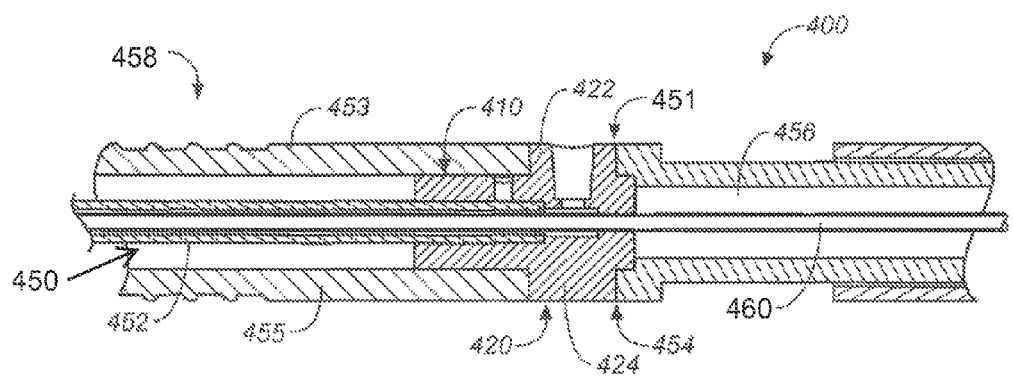

FIGS. 4A-4E, in which like elements share like reference numbers, are various views of a unitary endoseal of a stent graft delivery system. FIG. 4A is a side view, FIG. 4B is a top view, FIG. 4C is an longitudinal cross section side view, FIG. 4D is an longitudinal cross section side view showing the tip tube and middle member tube, and FIG. 4E is an longitudinal cross section side view showing the tip tube, middle member tube, and threaded assembly.

Referring to FIGS. 4A & 4B, the unitary endoseal 400 is for use in a stent graft delivery system having a tip tube; a middle member tube having middle member proximal end and defining a middle member lumen; and a threaded assembly, in which the threaded assembly defines a threaded assembly lumen, a first sidewall port, and a second sidewall port. The unitary endoseal 400 includes a longitudinal cylindrical endoseal body 410 and a transverse cylindrical endoseal body 420 transverse to the longitudinal cylindrical endoseal body 410. The transverse cylindrical endoseal body 420 has a first cylindrical portion 422 and a second cylindrical portion 424. A slit 426 communicates between the tapered flush port 428 and the middle portion of the endoseal lumen. The unitary endoseal 400 can be formed of any resilient material as desired for a particular application. In one embodiment, the unitary endoseal 400 is a resilient material such as urethane, silicone, or the like. In one embodiment, the resilient material has a Shore A durometer hardness of 60 to 70.

Referring to FIG. 4C, the longitudinal endoseal cylindrical body 410 defines an endoseal lumen 412 having a proximal portion 418, a middle portion 416, and a distal portion 414. The longitudinal endoseal cylindrical body 410 has a central axis 440 and the first cylindrical portion 422 defines a tapered flush port 428 tapering inward toward the central axis 440 with a partition 430 between the tapered flush port 428 and the middle portion 416 of the endoseal lumen 412. The partition 430 defines the slit 426 between the tapered flush port 428 and the middle portion 416 of the endoseal lumen 412. The middle portion 416 of the endoseal lumen 412 is in communication with the middle member lumen of the middle member tube.

In operation, the slit 426 is closed when the tapered flush port 428 is unoccupied, preventing debris or contamination from entering the middle portion 416 of the endoseal lumen 412 and the middle member lumen of the middle member tube. A flush connector (not shown) having a diameter greater than the diameter of the tapered flush port 428 near the central axis 440 can be used to open the slit 426. In one example, the flush connector is the male portion of a Luer fitting. As the flush connector is inserted into the tapered flush port 428, the radial force on the walls of the tapered flush port 428 expands the diameter of the tapered flush port 428 to conform to the flush connector. When the flush connector is fully inserted into the tapered flush port 428, the expansion of the tapered flush port 428 expands the partition 430, opening the slit 426. The walls of the tapered flush port 428 maintain a compressive radial force on the flush connector to provide a seal and maintain the flush connector in the tapered flush port 428. To flush the middle member lumen of the middle member tube before the stent graft delivery device is used with a patient, fluid can be provided through the flush connector, through the slit 426, through the middle portion 416 of the endoseal lumen 412 and through the middle member lumen of the middle member tube. The slit 426 closes when the flush connector is withdrawn from the tapered flush port 428.

Referring to FIG. 4D, the tip tube 460 is disposed in and longitudinally slideable within the proximal portion 418 of the endoseal lumen 412. The middle member proximal end 452 of the middle member tube 450 is disposed in the distal portion 414 of the endoseal lumen 412 and fixed to the longitudinal cylindrical endoseal body 410. In one embodiment, the middle member proximal end 452 is fixed to the longitudinal cylindrical endoseal body by an interference fit using frictional resistance to prevent separation between the middle member proximal end 452 and the longitudinal cylindrical endoseal body 410. In another embodiment, the middle member proximal end 452 is fixed to the longitudinal cylindrical endoseal body 410 with an adhesive. The longitudinal cylindrical endoseal body 410 can define an adhesive port 419 for application of the adhesive to the middle member proximal end 452 during manufacturing.

Referring to FIG. 4E, the first cylindrical portion 422 of the transverse cylindrical endoseal body 420 is disposed in the first sidewall port 451 defined by the first threaded tube portion 453 of the threaded assembly 458. The second cylindrical portion 424 of the transverse cylindrical endoseal body 420 is disposed in the second sidewall port 454 defined by the second threaded tube portion 455 of the threaded assembly 450. The longitudinal endoseal cylindrical body 410 is disposed in the threaded assembly lumen 456.

While specific embodiments are disclosed herein, various changes and modifications can be made without departing from the spirit and scope of the invention.

The invention claimed is:

1. A stent graft delivery system comprising:
a tip assembly having a tip tube;
a middle member tube having a middle member proximal end and defining a middle member lumen, the tip tube being disposed in and longitudinally slideable within the middle member lumen;
a sheath assembly having a sheath tube and a sheath handle operably connected to a sheath tube proximal end, the sheath tube defining a sheath lumen, the middle member tube being disposed in and longitudinally slideable within the sheath lumen;
a threaded assembly having an exterior thread, and defining a threaded assembly lumen, a first sidewall port, and a second sidewall port; and
a unitary endoseal having a longitudinal cylindrical endoseal body and a transverse cylindrical endoseal body transverse to the longitudinal cylindrical endoseal body, the longitudinal endoseal cylindrical body defining an endoseal lumen having a proximal portion, a middle portion, and a distal portion, the transverse cylindrical endoseal body having a first cylindrical portion and a second cylindrical portion, the first cylindrical portion defining a flush port transverse to the endoseal lumen;
wherein the tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first transverse cylindrical portion of the transverse cylindrical endoseal body is disposed in the first sidewall port of the threaded assembly, the second transverse cylindrical portion of the transverse cylindrical endoseal body is disposed in the second sidewall port of the threaded assembly, and the longitudinal endoseal cylindrical body is disposed in the threaded assembly lumen; and
the sheath handle engages the exterior thread of the threaded assembly in a first configuration to move the sheath tube longitudinally relative to the middle member tube and tip tube by rotation of the sheath handle and disengages the exterior thread of the threaded assembly in a second configuration to move the sheath tube longitudinally relative to the middle member tube and tip tube by longitudinal motion of the sheath handle.

2. The stent graft delivery system of claim 1 wherein:
the longitudinal endoseal cylindrical body has a central axis;
the flush port defined by the first cylindrical portion is a tapered flush port tapering inward toward the central axis with a partition between the tapered flush port and the middle portion of the endoseal lumen;
the partition defines a slit between the tapered flush port and the middle portion of the endoseal lumen, the middle portion of the endoseal lumen being in communication with the middle member lumen;
the slit is closed when the flush port is unoccupied; and
the slit is open when a flush connector is fully inserted into the flush port.

3. The stent graft delivery system of claim 1 wherein the unitary endoseal comprises a resilient material selected from the group consisting of urethane and silicone.

4. The stent graft delivery system of claim 1 wherein the unitary endoseal comprises a resilient material having a Shore A durometer hardness of 60 to 70.

5. The stent graft delivery system of claim 1 wherein the middle member proximal end is fixed to the longitudinal cylindrical endoseal body by friction between the middle member proximal end and the longitudinal cylindrical endoseal body.

6. The stent graft delivery system of claim 1 wherein the middle member proximal end is fixed to the longitudinal cylindrical endoseal body with an adhesive.

7. The stent graft delivery system of claim 1 wherein the tip tube defines a guide wire lumen.

8. The stent graft delivery system of claim 1 further comprising a tip handle operably connected to a tip tube proximal end.

9. The stent graft delivery system of claim 1 wherein:
the threaded assembly has a first threaded tube portion and a second threaded tube portion;
the first threaded tube portion defines the first sidewall port; and
the second threaded tube portion defines the second sidewall port.

10. A unitary endoseal for use in a stent graft delivery system having a tip tube; a middle member tube having middle member proximal end and defining a middle member lumen; and a threaded assembly, the threaded assembly defining a threaded assembly lumen, a first sidewall port, and a second sidewall port; the unitary endoseal comprising:
a longitudinal cylindrical endoseal body, the longitudinal endoseal cylindrical body defining an endoseal lumen having a proximal portion, a middle portion, and a distal portion; and
a transverse cylindrical endoseal body transverse to the longitudinal cylindrical endoseal body, the transverse cylindrical endoseal body having a first cylindrical portion and a second cylindrical portion, the first cylindrical portion defining a flush port transverse to the endoseal lumen;

wherein the tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first cylindrical portion of the transverse cylindrical endoseal body is disposed in the first sidewall port of the threaded assembly, the second cylindrical portion of the transverse cylindrical endoseal body is disposed in the second sidewall port of the threaded assembly, and the longitudinal endoseal cylindrical body is disposed in the threaded assembly lumen.

11. The unitary endoseal of claim 10 wherein:
the longitudinal endoseal cylindrical body has a central axis;
the flush port defined by the first cylindrical portion is a tapered flush port tapering inward toward the central axis with a partition between the tapered flush port and the middle portion of the endoseal lumen;
the partition defines a slit between the tapered flush port and the middle portion of the endoseal lumen, the middle portion of the endoseal lumen being in communication with the middle member lumen;
the slit is closed when the tapered flush port is unoccupied; and
the slit is open when a flush connector is fully inserted into the tapered flush port.

12. The unitary endoseal of claim 10 wherein the unitary endoseal comprises a resilient material selected from the group consisting of urethane and silicone.

13. The unitary endoseal of claim 10 wherein the unitary endoseal comprises a resilient material having a Shore A durometer hardness of 60 to 70.

14. The unitary endoseal of claim 10 wherein the middle member proximal end is fixed to the longitudinal cylindrical endoseal body by friction between the middle member proximal end and the longitudinal cylindrical endoseal body.

15. The unitary endoseal of claim 10 wherein the middle member proximal end is fixed to the longitudinal cylindrical endoseal body with an adhesive.

16. A stent graft delivery system comprising:
a tip assembly having a tip tube;
a middle member tube having a middle member proximal end and defining a middle member lumen, the tip tube being disposed in and longitudinally slideable within the middle member lumen;
a sheath assembly having a sheath tube and a sheath handle operably connected to a sheath tube proximal end, the sheath tube defining a sheath lumen, the middle member tube being disposed in and longitudinally slideable within the sheath lumen;
a threaded assembly having an exterior thread, and defining a threaded assembly lumen, a first sidewall port, and a second sidewall port; and
a unitary endoseal having a longitudinal cylindrical endoseal body and a transverse cylindrical endoseal body transverse to the longitudinal cylindrical endoseal body, the longitudinal endoseal cylindrical body having a central axis and defining an endoseal lumen having a proximal portion, a middle portion, and a distal portion, the transverse cylindrical endoseal body having a first cylindrical portion and a second cylindrical portion, the first cylindrical portion defining a tapered flush port tapering inward toward the central axis with a partition between the tapered flush port and the middle portion of the endoseal lumen, the partition defining a slit between the tapered flush port and the middle portion of the endoseal lumen, the middle portion of the endoseal lumen being in communication with the middle member lumen;
wherein the tip tube is disposed in and longitudinally slideable within the proximal portion of the endoseal lumen, the middle member proximal end of the middle member tube is disposed in the distal portion of the endoseal lumen and fixed to the longitudinal cylindrical endoseal body, the first cylindrical portion of the transverse cylindrical endoseal body is disposed in the first sidewall port of the threaded assembly, the second cylindrical portion of the transverse cylindrical endoseal body is disposed in the second sidewall port of the threaded assembly, and the longitudinal endoseal cylindrical body is disposed in the threaded assembly lumen; the slit is closed when the flush port is unoccupied; and the slit is open when a flush connector is fully inserted into the flush port.

17. The stent graft delivery system of claim 16 wherein the unitary endoseal comprises a resilient material selected from the group consisting of urethane and silicone.

18. The stent graft delivery system of claim 16 wherein the unitary endoseal comprises a resilient material having a Shore A durometer hardness of 60 to 70.

19. The stent graft delivery system of claim 16 wherein the middle member proximal end is fixed to the longitudinal cylindrical endoseal body by friction between the middle member proximal end and the longitudinal cylindrical endoseal body.

20. The stent graft delivery system of claim 16 wherein the middle member proximal end is fixed to the longitudinal cylindrical endoseal body with an adhesive.

* * * * *